(12) United States Patent
Addison et al.

(10) Patent No.: US 8,364,225 B2
(45) Date of Patent: Jan. 29, 2013

(54) ESTIMATING TRANSFORM VALUES USING SIGNAL ESTIMATES

(75) Inventors: Paul Stanley Addison, Edinburgh (GB); James Nicholas Watson, Dunfermline (GB); Braddon M. Van Slyke, Arvada, CO (US)

(73) Assignee: Nellcor Puritan Bennett Ireland, Mervue, Galway ( * ) Notice: Subject to any disclaimer, the term of this patent is extended or adjusted under 35 U.S.C. 154(b) by 924 days.

(21) Appl. No.: 12/469,491

(22) Filed: May 20, 2009

(65) Prior Publication Data

US 2010/0298676 A1    Nov. 25, 2010

(51) Int. Cl.
| A61B 5/00 | (2006.01) |
| A61B 5/02 | (2006.01) |
| A61B 5/08 | (2006.01) |
| G01N 33/48 | (2006.01) |
| G01N 33/50 | (2006.01) |

(52) U.S. Cl. ........... 600/336; 702/19; 600/502; 600/529
(58) Field of Classification Search .................. 600/323, 600/310, 480, 485, 502, 529, 336; 708/400; 702/19
See application file for complete search history.

(56) References Cited

U.S. PATENT DOCUMENTS

| 4,289,141 A | 9/1981 | Cormier |
| 5,439,483 A | 8/1995 | Duong-Van |
| 5,590,650 A | 1/1997 | Genova |
| 5,632,272 A | 5/1997 | Diab et al. |
| 5,778,881 A | 7/1998 | Sun et al. |
| 5,795,304 A | 8/1998 | Sun et al. |
| 5,797,840 A | 8/1998 | Akselrod et al. |
| 5,827,195 A | 10/1998 | Lander |
| 5,967,995 A | 10/1999 | Shusterman et al. |
| 6,002,952 A | 12/1999 | Diab et al. |
| 6,036,653 A | 3/2000 | Baba et al. |
| 6,094,592 A | 7/2000 | Yorkey et al. |
| 6,095,984 A | 8/2000 | Amano et al. |
| 6,117,075 A | 9/2000 | Barnea |
| 6,129,675 A | 10/2000 | Jay |
| 6,135,966 A | 10/2000 | Ko |
| 6,171,257 B1 | 1/2001 | Weil et al. |
| 6,171,258 B1 | 1/2001 | Karakasoglu et al. |
| 6,208,951 B1 | 3/2001 | Kumar et al. |
| 6,293,915 B1 | 9/2001 | Amano et al. |

(Continued)

FOREIGN PATENT DOCUMENTS

| JP | 09-084776 | 3/1997 |
| WO | WO 01/25802 | 4/2001 |

(Continued)

OTHER PUBLICATIONS

Addison, Paul S., The Illustrated Wavelet Transform Handbook, Taylor & Francis Group, 2002.

(Continued)

*Primary Examiner* — Brian Szmal

(57) ABSTRACT

According to embodiments, estimated values for a signal transform may be generated using estimated values for the signal. Signal parameters may then be determined based on the estimated signal transform. A first portion of a signal may be obtained. A second portion of the signal may be estimated. The second portion of the signal may correspond to a portion of the that is unknown, that is not yet available and/or that is obscured by noise and/or artifacts. A transform (e.g., a continuous wavelet transform) of both of the signal portions may be performed. One or more parameters corresponding to the signal may then be determined from transformed signal.

20 Claims, 13 Drawing Sheets

U.S. PATENT DOCUMENTS

| | | |
|---|---|---|
| 6,325,761 B1 | 12/2001 | Jay |
| 6,361,501 B1 | 3/2002 | Amano et al. |
| 6,393,311 B1 | 5/2002 | Edgar, Jr. et al. |
| 6,430,525 B1 | 8/2002 | Weber et al. |
| 6,561,986 B2 | 5/2003 | Baura et al. |
| 6,608,934 B2 | 8/2003 | Scheirer et al. |
| 6,654,623 B1 | 11/2003 | Kästle |
| 6,810,277 B2 | 10/2004 | Edgar, Jr. et al. |
| 6,931,269 B2 | 8/2005 | Terry |
| 6,999,904 B2 | 2/2006 | Weber et al. |
| 7,001,337 B2 | 2/2006 | Dekker |
| 7,020,507 B2 | 3/2006 | Scharf et al. |
| 7,035,679 B2 | 4/2006 | Addison et al. |
| 7,043,293 B1 | 5/2006 | Baura |
| 7,054,453 B2 | 5/2006 | Causevic et al. |
| 7,054,454 B2 | 5/2006 | Causevic et al. |
| 7,079,888 B2 | 7/2006 | Oung et al. |
| 7,171,269 B1 | 1/2007 | Addison et al. |
| 7,173,525 B2 | 2/2007 | Albert |
| 7,203,267 B2 | 4/2007 | De Man et al. |
| 7,225,013 B2 | 5/2007 | Geva et al. |
| 7,254,500 B2 | 8/2007 | Makeig et al. |
| 7,289,835 B2 | 10/2007 | Mansfield et al. |
| 7,499,835 B2 | 3/2009 | Weber et al. |
| 7,515,949 B2 | 4/2009 | Norris |
| 7,519,488 B2 | 4/2009 | Fu et al. |
| 7,523,011 B2 | 4/2009 | Akiyama et al. |
| 2003/0163057 A1 | 8/2003 | Flick et al. |
| 2005/0043616 A1 | 2/2005 | Chinchoy |
| 2006/0209631 A1 | 9/2006 | Melese et al. |
| 2006/0211930 A1 | 9/2006 | Scharf et al. |
| 2006/0229519 A1 | 10/2006 | Fujiwara et al. |
| 2006/0258921 A1 | 11/2006 | Addison et al. |
| 2006/0265022 A1 | 11/2006 | John et al. |
| 2007/0021673 A1 | 1/2007 | Arbel et al. |
| 2007/0073120 A1 | 3/2007 | Li et al. |
| 2007/0073124 A1 | 3/2007 | Li et al. |
| 2007/0167694 A1 | 7/2007 | Causevic et al. |
| 2007/0167851 A1 | 7/2007 | Vitali et al. |
| 2007/0282212 A1 | 12/2007 | Sierra et al. |
| 2008/0045832 A1 | 2/2008 | McGrath |
| 2008/0082018 A1 | 4/2008 | Sackner et al. |
| 2008/0214903 A1 | 9/2008 | Orbach |
| 2008/0243021 A1 | 10/2008 | Causevic et al. |

FOREIGN PATENT DOCUMENTS

| | | |
|---|---|---|
| WO | WO 01/62152 | 8/2001 |
| WO | WO 03/055395 | 7/2003 |
| WO | WO 2004/105601 | 12/2004 |
| WO | WO 2005/096170 | 10/2005 |
| WO | WO 2006/085120 | 8/2006 |

OTHER PUBLICATIONS

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Leonard, Paul A., Douglas, J. Graham, Grubb, Neil R., Clifton, David, Addison, Paul S., Watson, James N., "A Fully Automated Algorithm for the Determination of Respiratory Rate from the Photoplethysmogram," Journal of Clinical Monitoring and Computing, 2006.

Leonard, Paul A., Clifton, David, Addison, Paul S., Watson, James N., Beattie, Tom "An Automated Algorithm for Determining Respiratory Rate by Photoplethtsmogram in Children," Acta Paediatricia, 2006; 95: 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Application," Journal of the Institute of Electronics, Information and Communication Engineers, vol. 76, No. 5, May 1993, pp. 518-528.

ESTIMATING TRANSFORM VALUES USING SIGNAL ESTIMATES

SUMMARY

The present disclosure is related to signal processing systems and methods, and more particularly, to systems and methods for estimating values in a signal transform using estimated values for the signal. Parameters related to the signal may be determined based on the estimated signal transform.

In an embodiment, a signal transform (e.g., a continuous wavelet transform) may contain one or more regions in which the values of the transform may be unknown or erroneous. These unknown or erroneous transform values may be replaced with estimated transform values. The estimated transform values may be generated by estimating values for the signal used to compute the transform. The estimated signal values may replace portions of the signal that are unknown, that are not yet available (i.e., future signal values) and/or that are obscured by noise and/or artifacts.

In an embodiment, a signal transform may contain a significant amount of erroneous transform values in a region around an end point of the signal. This region may be referred to as an "edge effect" region. When the transform is computed within the edge effect region, the end point of the signal may appear within the computation as a sharp discontinuity in the signal. This apparent sharp discontinuity in the signal may adversely affect the computed values of the transform in this region. In order to reduce the erroneous transform values in this edge effect region, signal values may be estimated for the, as yet unknown, portion of the signal beyond the end point. The estimated signal values may then be used to compute the transform of the signal. In an embodiment, the estimated signal values may be set to a constant value such as, for example, a current signal value or a mean signal value. In an embodiment, the estimated signal values may be an extrapolated estimate or fitted curve (i.e., a functional estimate) of the signal. In an embodiment, known signal types (e.g., a PPG signal) may be estimated based on characteristic values of the signal and/or information about the origin of the signal.

In an embodiment, the transform may be a continuous wavelet transform. A continuous wavelet transform may be performed by computing a convolution (or any other suitable cross-correlation) of the signal with wavelets at various scales. Within an edge effect region (or any other similar region) any computed transform values may be incomplete because the signal values required to fully resolve the transform for a particular time period may not be known or available. At higher scales the smaller wavelet scale sizes may result in a smaller edge effect region. At lower scales the larger wavelet scale sizes may result in a larger edge effect region. The size of the estimated signal portions may therefore depend on the scales at which the transform is computed.

In an embodiment, the transformed signal may be a photoplethysmograph (PPG) signal. A first portion of the PPG signal may be obtained. The first portion of the PPG signal may have an end point because additional signal values have not yet arrived. A second portion of the PPG signal may be estimated. The second portion of the PPG signal may correspond to a portion of the signal beyond the end point of the first signal portion. A transform (e.g., a continuous wavelet transform) of the signal portions may be performed. One or more biological parameters may be determined based on the transformed signal including, for example, blood oxygen saturation level, respiration rate, respiration effort metric, pulse rate, and/or blood pressure.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
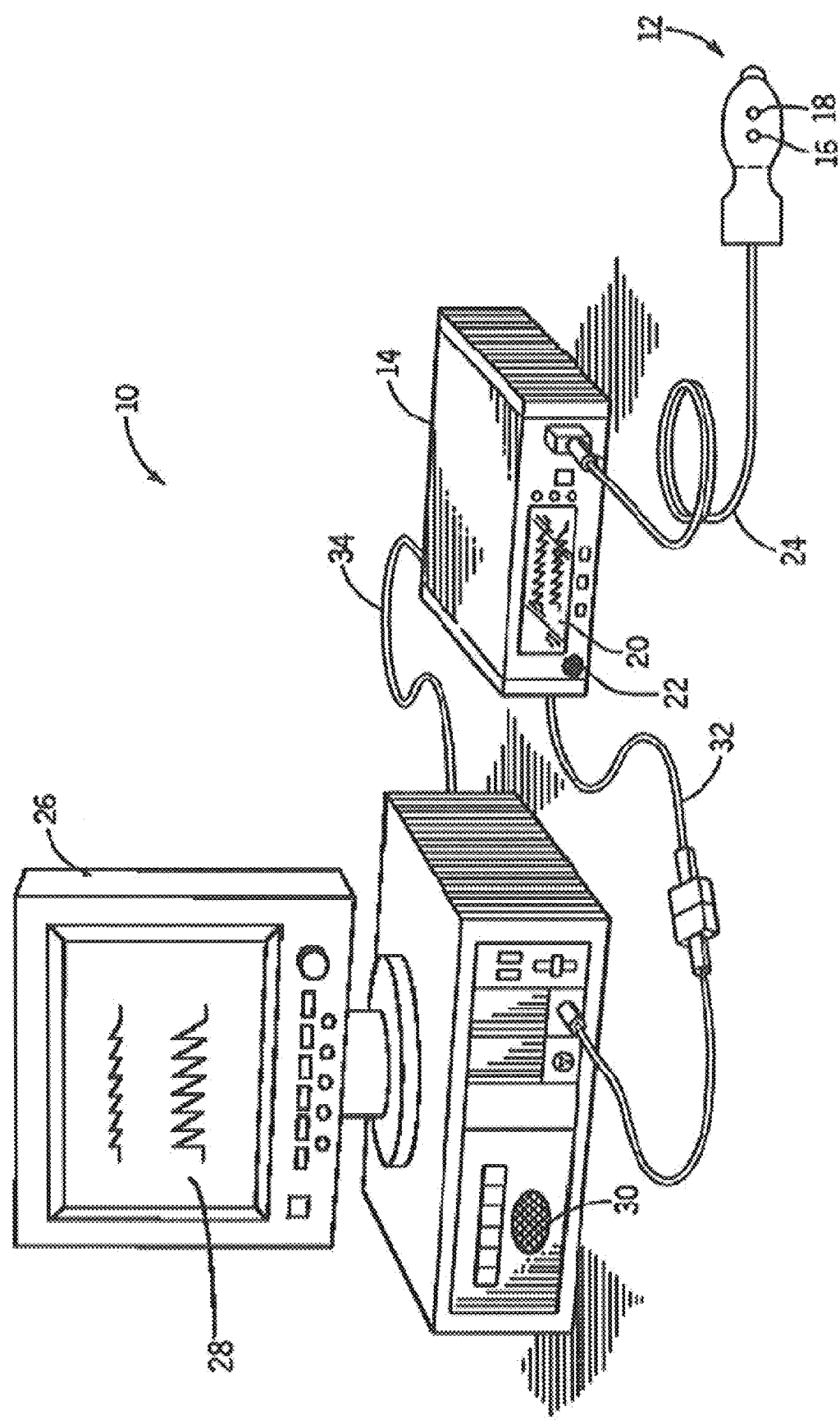
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof a scaled version of a log taken thereof etc.) may be referred to as the photoplethysmograph (PPG) signal. In addition, the term "PPG signal" as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I=\log I_o-(s\beta_o+(1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R)+(1-s)\beta_r(\lambda_R)}{s\beta_o(\lambda_{IR})+(1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR})-\beta_r(\lambda_{IR})) - \frac{d\log I(\lambda_{IR})}{dt}(\beta_o(\lambda_R)-\beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2,\lambda)}{I(t_1,\lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1,\lambda_R)}{I(t_2,\lambda_R)}\right)}{\log\left(\frac{I(t_1,\lambda_{IR})}{I(t_2,\lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR})-\beta_r(\lambda_{IR})) - \beta_o(\lambda_R)+\beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2,\lambda_R)-I(t_1,\lambda_R)}{I(t_1,\lambda_R)}}{\frac{I(t_2,\lambda_{IR})-I(t_1,\lambda_{IR})}{I(t_1,\lambda_{IR})}} \quad (7)$$

$$= \frac{[I(t_2,\lambda_R)-I(t_1,\lambda_R)]I(t_1,\lambda_{IR})}{[I(t_2,\lambda_{IR})-I(t_1,\lambda_{IR})]I(t_1,\lambda_R)}$$

$$= R$$

which defines a cluster of points whose slope of y versus x will give R where $$x(t)=[I(t_2,\lambda_{IR})-I(t_1,\lambda_{IR})]I(t_1,\lambda_{IR})$$

$$y(t)=[I(t_2,\lambda_R)-I(t_1,\lambda_R)]I(t_1,\lambda_{IR})$$

$$y(t)=Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
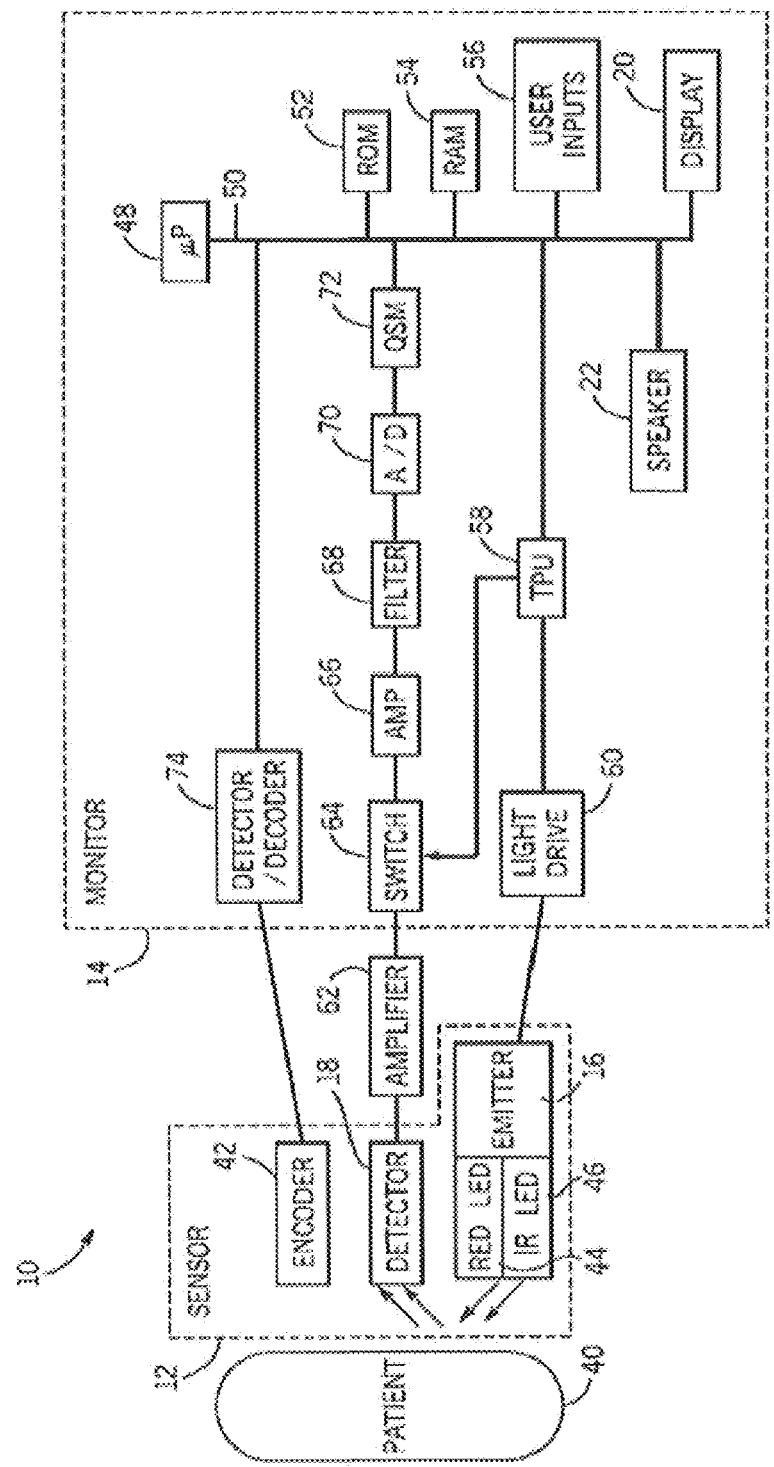
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patients tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patients tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patients tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g. electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right)dt \qquad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \quad (10)$$

where '$|\,|$' is the modulus operator. The scalogram may be rescaled for useful purposes. One common rescaling is defined as $$S_R(a, b) = \frac{|T(a, b)|^2}{a} \quad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
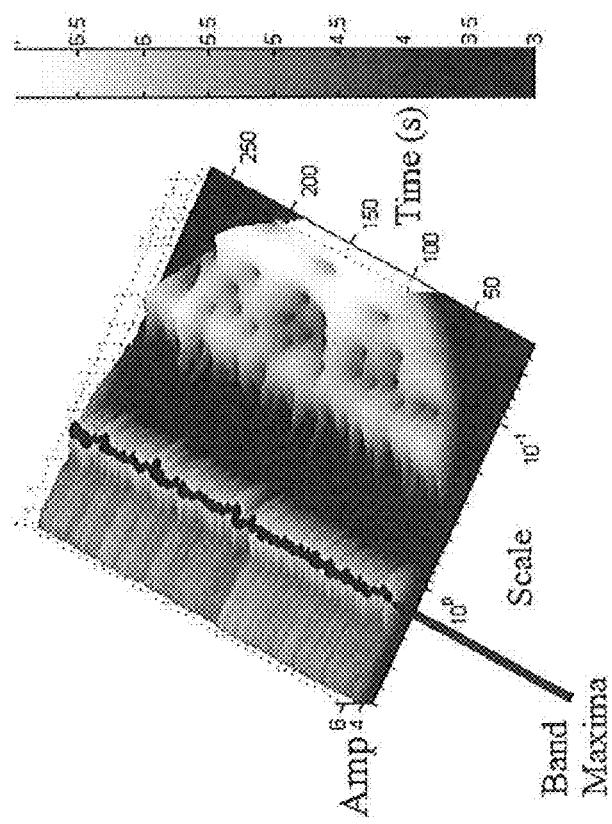
FIGS. 3(a) and 3(b) show illustrative views of a scalogram derived from a PPG signal in accordance with an embodiment.
Figure 3A:
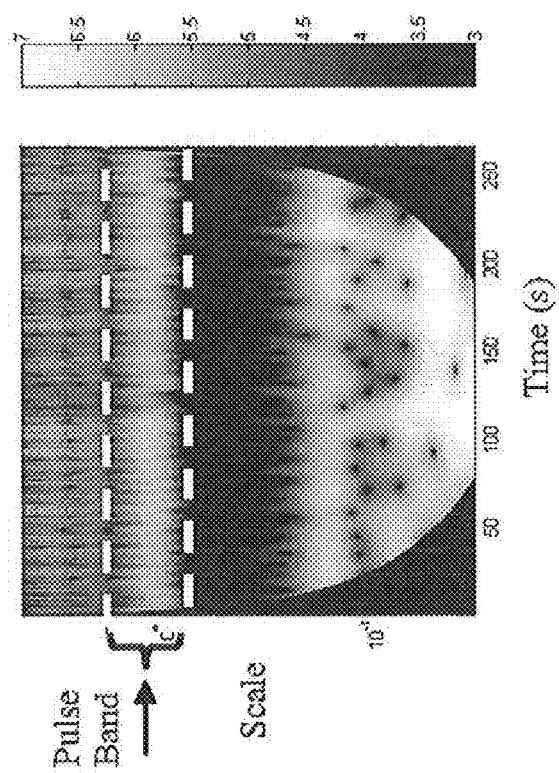

Pertinent repeating features in a signal give rise to a time-scale band in wavelet space or a resealed wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable resealing of the scalogram, such as that given in equation (11), the ridges found in wavelet space may be related to the instantaneous frequency of the signal. In this way, the pulse rate may be obtained from the PPG signal. Instead of resealing the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
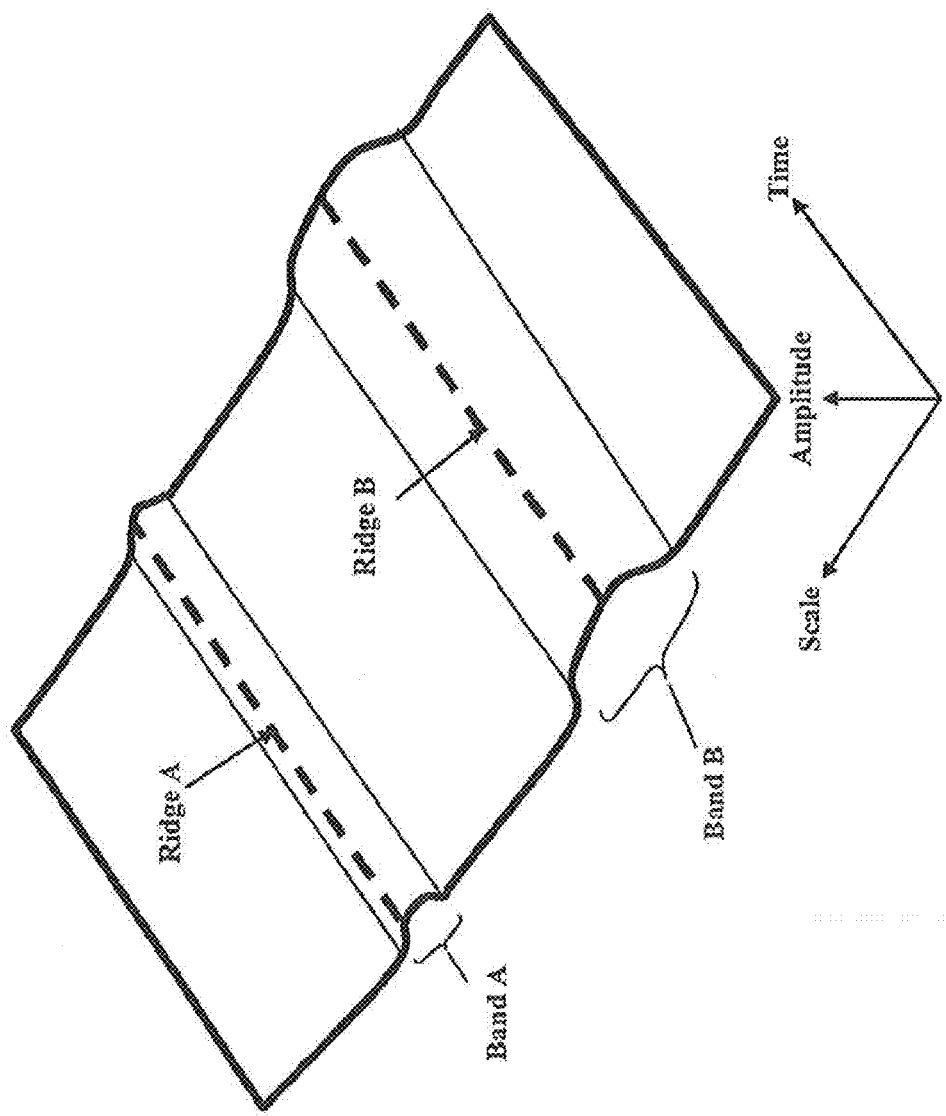
FIG. 3(c) shows an illustrative scalogram derived from a signal containing two pertinent components in accordance with an embodiment.
Figure 3D:
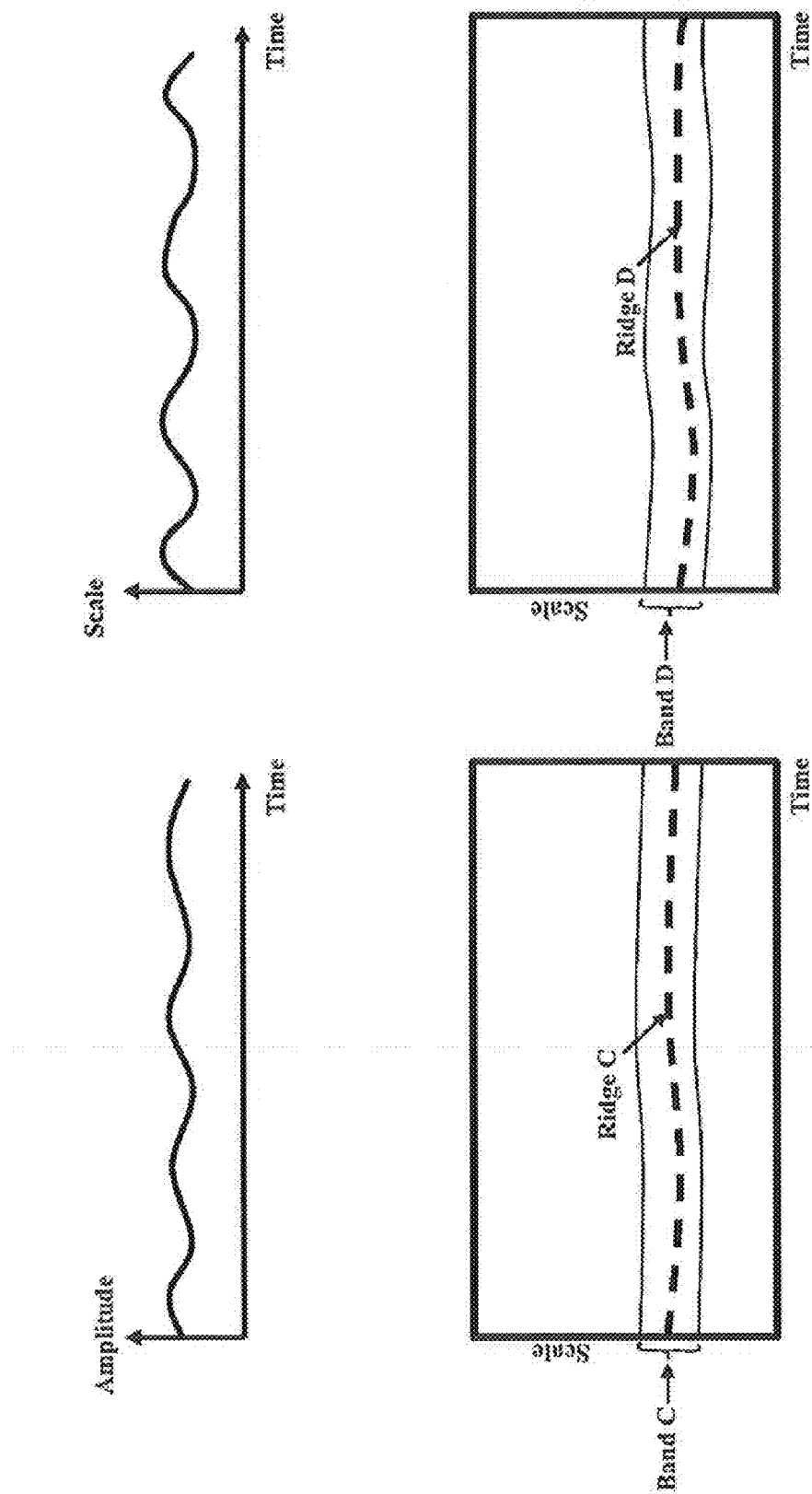
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a resealed wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_{0}^{\infty} T(a,b) \psi_{a,b}(t) \frac{da\,db}{a^2} \quad (16)$$

where $C_g$ is a scalar value known as the admissibility constant. It is wavelet type dependent and may be calculated from:

$$C_g = \int_{0}^{\infty} \frac{|\hat{\psi}(f)|^2}{f} df \quad (17)$$

Figure 3E:
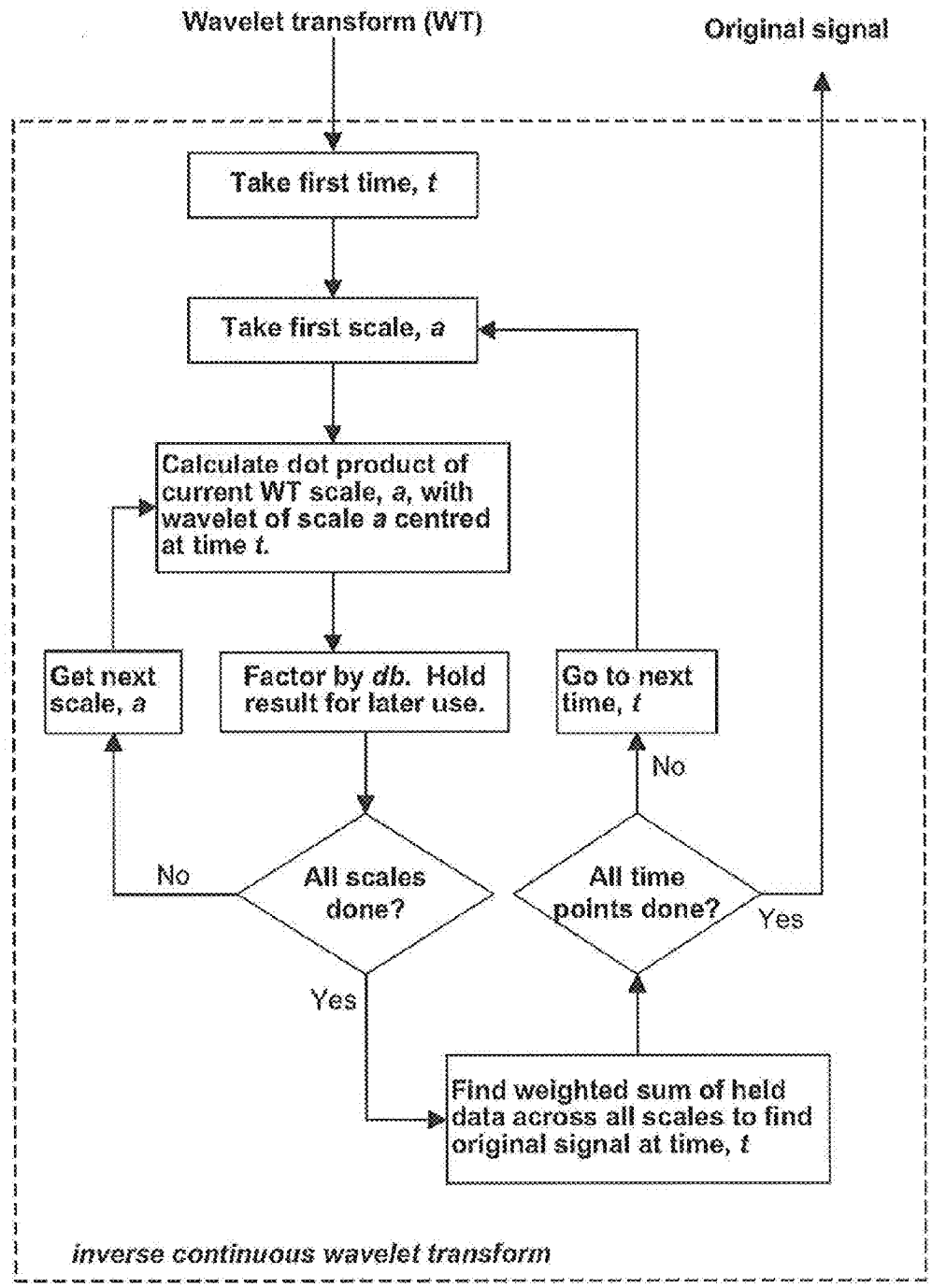
FIGS. 3(e) and 3(f) are flow charts of illustrative steps involved in performing an inverse continuous wavelet transform in accordance with embodiments.
Figure 3F:
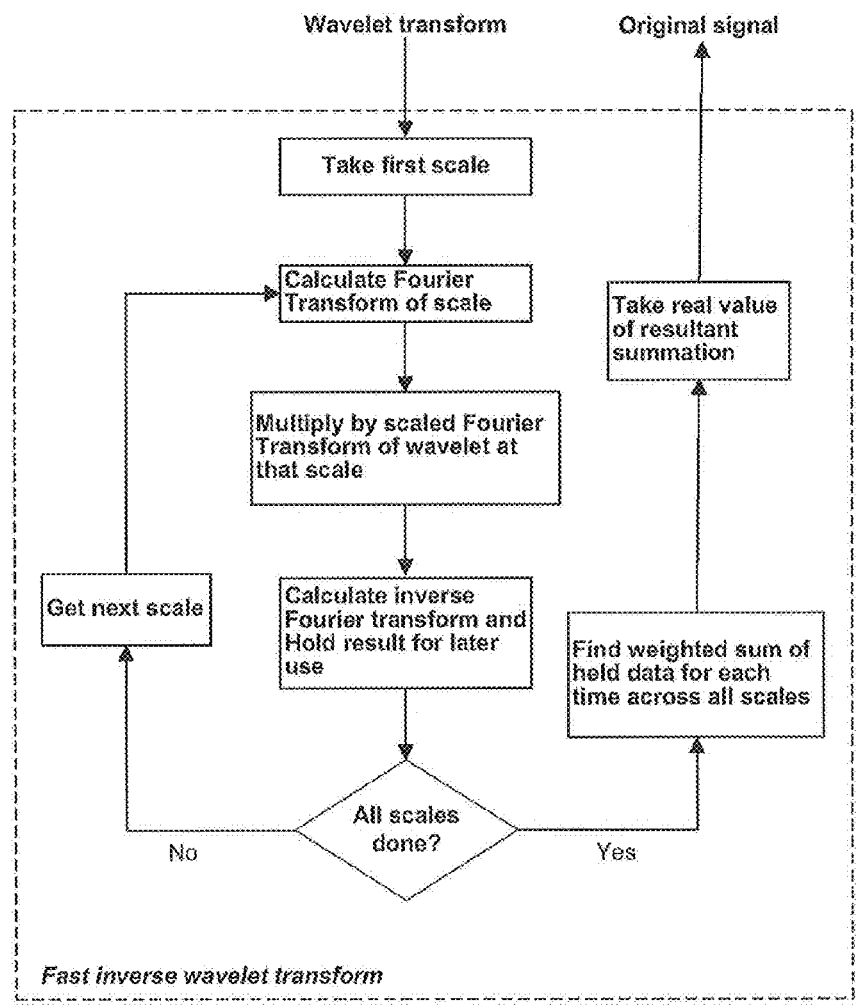

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
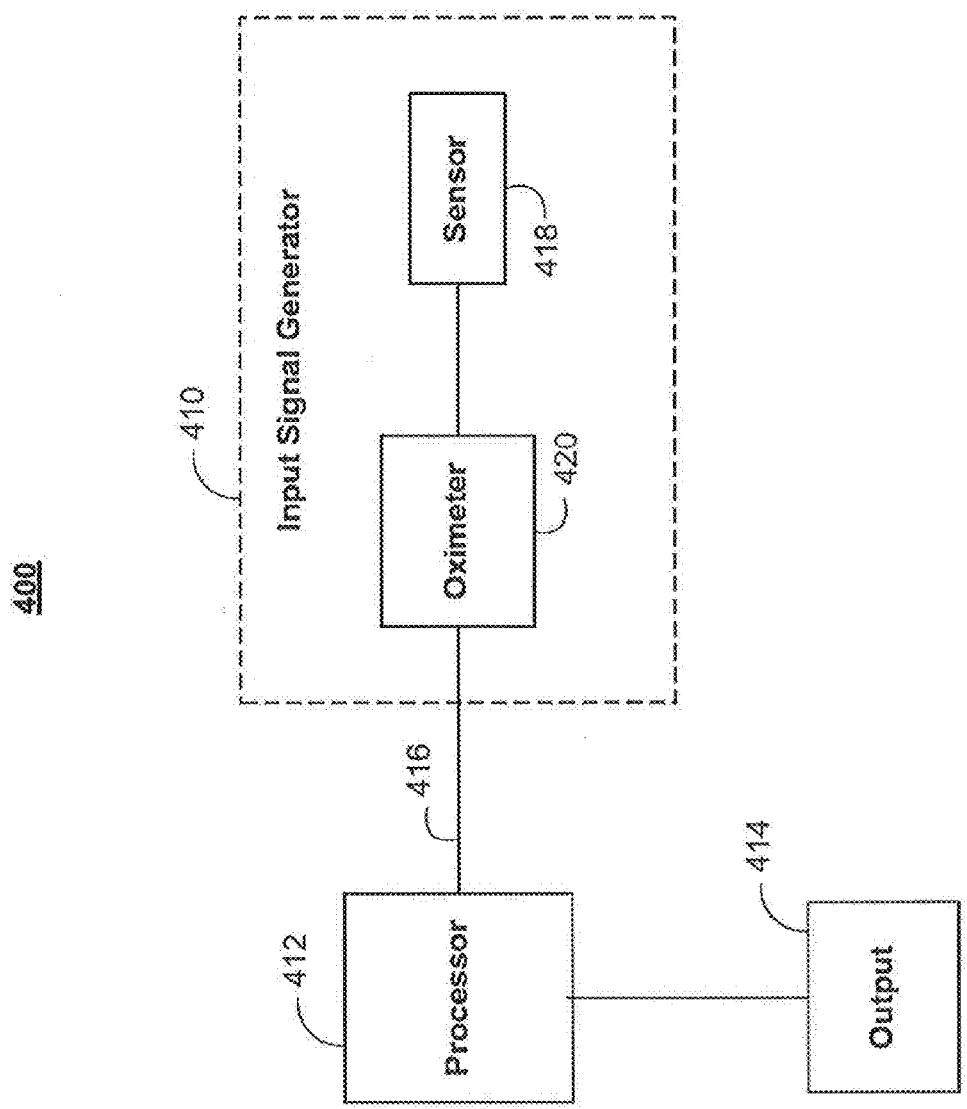
FIG. 4 is a block diagram of an illustrative continuous wavelet processing system in accordance with some embodiments.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Figure 5:
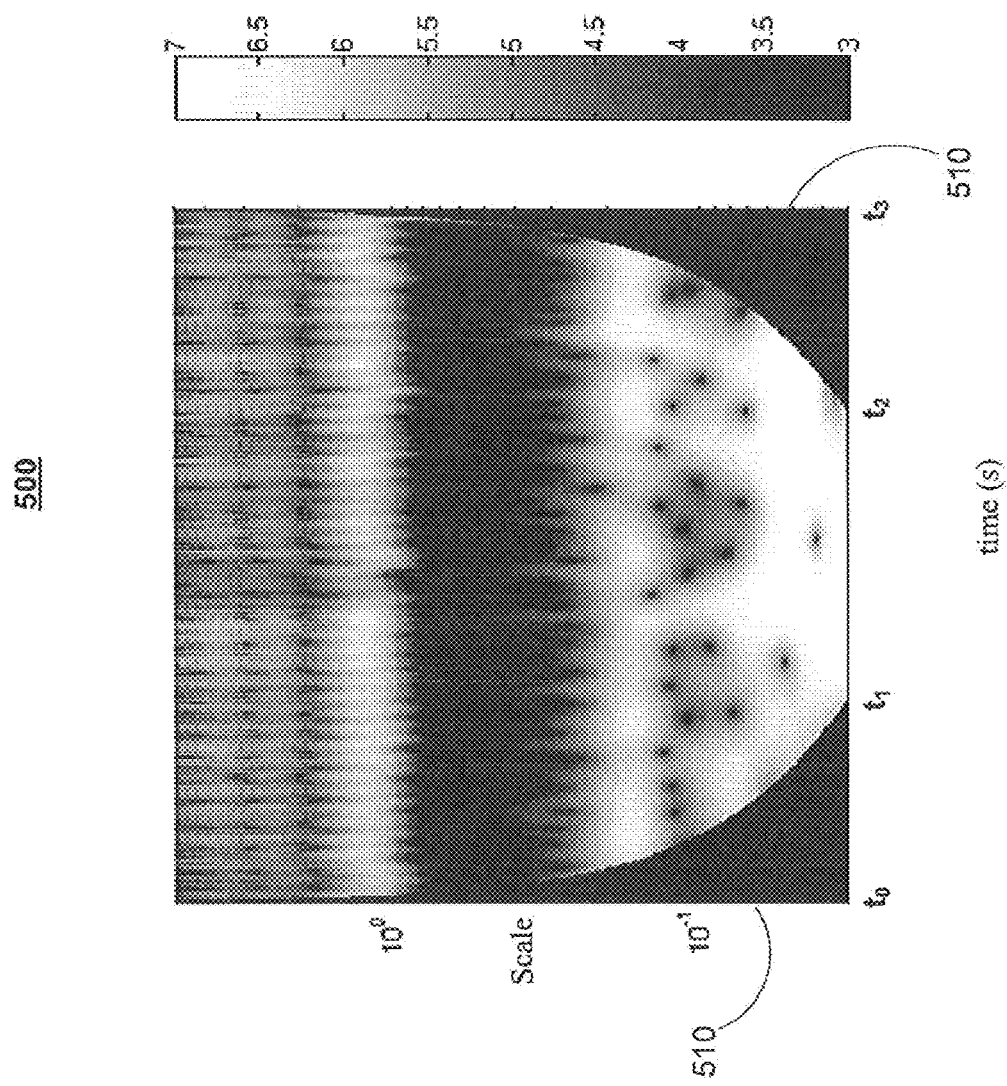
FIG. 5 is an illustrative plot of a scalogram in accordance with some embodiments.

FIG. 5 shows a plot of an illustrative scalogram 500. For example, scalogram 500 may be generated from a PPG signal using the same method (e.g., using a continuous wavelet transform) that was used to derive the scalograms shown in FIGS. 3(a), 3(b), and 3(c). The scalogram of the transform of any suitable signal may be generated or otherwise obtained using, for example a processor such as processor 412 (FIG. 4) or microprocessor 48 (FIG. 2).

Scalogram 500 includes edge effect regions 510 (also referred to herein as wedge regions). As described above, a wavelet transform (e.g., a continuous wavelet transform) of a signal may be performed by computing a convolution (or any other suitable cross-correlation) of the signal with wavelets at various scales. Irrespective of the particular method used to compute the transform, due to the finite extent of the signal, edge effects will be present. Within the edge effect region of the scalogram any computed transform values may be incomplete because the signal values required to fully resolve the transform for a particular time period may not be known or available. For example, the unknown signal values may correspond to portions of the signal before known signal values (i.e., signal values preceding the start of signal monitoring) or to portion of the signal after known signal values (i.e., signal values that have not yet arrived). The edge effect region may be longer at larger scales because it takes longer (i.e., requires a larger signal portion) to fully resolve the wavelet transform of a signal at larger scales.

Scalogram 500 illustrates the transform of a signal portion that spans from time $t_0$ to $t_3$. Edge effect regions 510 of scalogram 500 may contain erroneous energy values resulting from apparent sharp discontinuities at either end of the signal portion. This is because the wavelet transform can only be computed using the known signal portion values. Computationally the effect of the signal ends on the transform may be equivalent to setting the unavailable signal values to zero. This large discontinuity at the signal ends may result in the sharp discontinuities in scalogram 500 that defines edge effect regions 510.

At higher scales (e.g., the top portion of scalogram 500) the smaller wavelet scale sizes may result in a smaller edge effect region. At lower scales (e.g., the bottom portion of scalogram 500) the larger wavelet scale sizes may result in a larger edge effect region. Similarly, degrees of resolution to which the wavelet transform of the signal is computed may also effect the size of the edge effect region. A lower resolution may result in a smaller edge effect region, while a higher resolution may result in a larger edge effect region. For discrete wavelets, having a finite extent, the whole wavelet may be used. For continuous wavelets (e.g., the Mortlet wavelet), which have a theoretically infinite extent, the degree of resolution may define the point at which the error between the true wavelet transform and the computed wavelet transform is acceptable for the purposes of the computation. In an embodiment, the Morlet wavelet may be cut-off approximately three standard deviations from the center of the Gaussian window forming part of the wavelet function. The degree of resolution may be determined or adjusted by a user or patient using, e.g., using user inputs 56 (FIG. 2).

While the edge effect regions discussed herein are generally described as occurring at the end of a signal, it should be understood that the edge effect region may refer to any region of the scalogram in which there are erroneous values resulting from large discontinuities in the signal. For example, an edge effect region may also occur when there is a temporary loss of signal or where there is a large amount of noise and/or artifacts that disrupt the signal.

Figure 6:
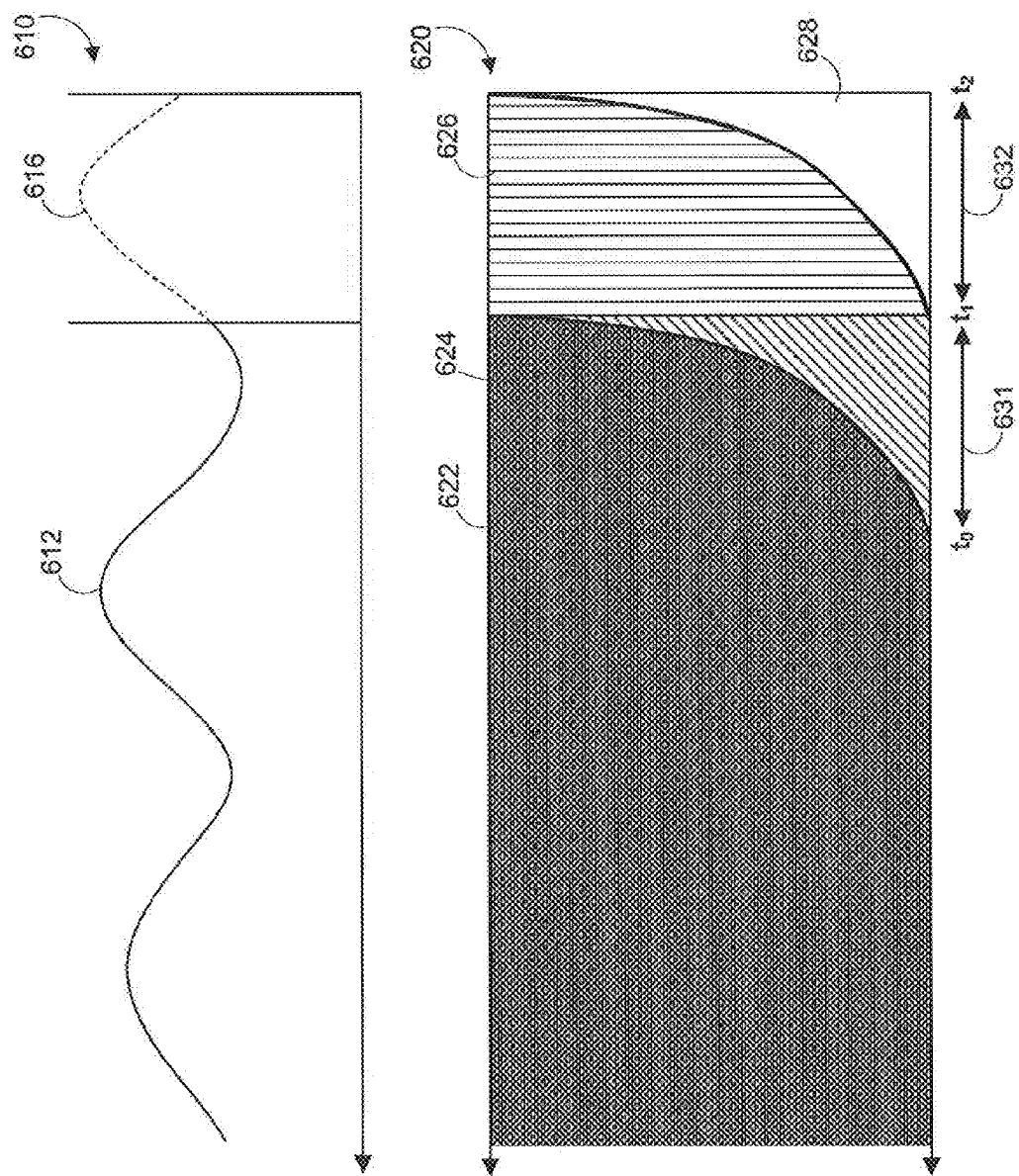
FIG. 6 is an illustrative plot of a signal and a scalogram generated from that signal that schematically illustrates a process for estimating values for a transform using a signal estimate in accordance with some embodiments.

FIG. 6 shows a plot of an illustrative signal 610 and an illustrative scalogram 620 generated from signal 610 and that schematically illustrates a process for estimating values for a transform using a signal estimate. Scalogram 620 may be derived from signal 610 using the same method (e.g., using a continuous wavelet transform) that was used to derive the scalograms shown in FIGS. 3(a), 3(b), 3(c), and 5. Signal portion 612 is a portion of a known signal that ends at time $t_1$. Signal portion 612 may be, for example, a PPG signals obtained from a patient, such as patient 40 (FIG. 2), using a sensor such as sensor 12 (FIG. 1). Scalogram portion 622 is a portion of scalogram 620 that was generated from signal portion 612. Scalogram portion 622 includes edge effect region 624 which was generated as a result of the end of signal portion 612 at time $t_1$.

As illustrated in FIG. 6, estimated transform values for edge effect region 624 of scalogram 620 may be generated using values estimated for the, as yet unknown, portion of signal 610 after time $t_1$ (i.e. signal portion 616). Generating estimated transform values using an estimated signal portion may limit the effect of the discontinuity at the end of signal portion 612 on edge effect region 624 of scalogram 620. The estimated values of signal portion 616 may then be replaced and/or updated as new values for signal 610 are obtained. Similarly, the estimated transform values of edge effect region 624 of scalogram 620 may also be replaced and/or updated based on the new values obtained for signal 610.

The estimated values for signal 610 may be represented by estimated signal portion 616. Estimated signal portion 616 may be determined based on the values of signal portion 612. For example, estimated signal portion 616 may be estimated as a constant value, as an extrapolation of previous signal values, or as a known signal type having determined characteristic values. An illustrative process for determining values for an estimated signal portion is described below with respect to FIG. 8. The transform of signal 610 may be computed using the values of estimated signal portion 616 and this transform may be used to generate scalogram 620 including estimated edge effect region 624. Estimated edge effect region 624 may be generated from the values of estimated signal portion 616. As illustrated, the length of estimated signal portion 616 (i.e., the period of time between $t_1$ and $t_2$) may be approximately equal to the maximum length of estimated edge effect region 624 (i.e., the period of time between $t_0$ and $t_1$). In this example, the entire edge effect region 624 (i.e., the period of time between $t_0$ and $t_1$) is estimated up to and including the largest wavelet scale sizes (i.e., at the lowest scales) illustrated in scalogram 600. If estimated transform values are only needed for higher scales (i.e., smaller scale sizes), a shorter estimated signal portion may be used to generate an estimated scalogram portion that provides estimated transform values for the necessary scales. As described above with respect to the scalograms shown in FIGS. 3(a), 3(b), and 3(c), scalogram 600 including estimated edge effect region 624 may be processed to determine one or more parameters or characteristics of signal 610. Replacing the erroneous values of edge effect region 624 with estimated values may simplify and/or improve the processing of scalogram 600 to determine these parameters. For example, a PPG signal transformed in this manner may be used to determine a blood oxygen saturation value, a respiration rate, a respiration effort metric, or another suitable biological parameter. In an embodiment, in addition to estimating edge effect region 624 based on estimated signal portion 616, scalogram portion 626 may also be estimated based on estimated signal portion 616. Furthermore, estimated signal portion 616 may be extended beyond time $t_2$ to estimate scalogram portion 626 or additional scalogram portions.

Figure 7:
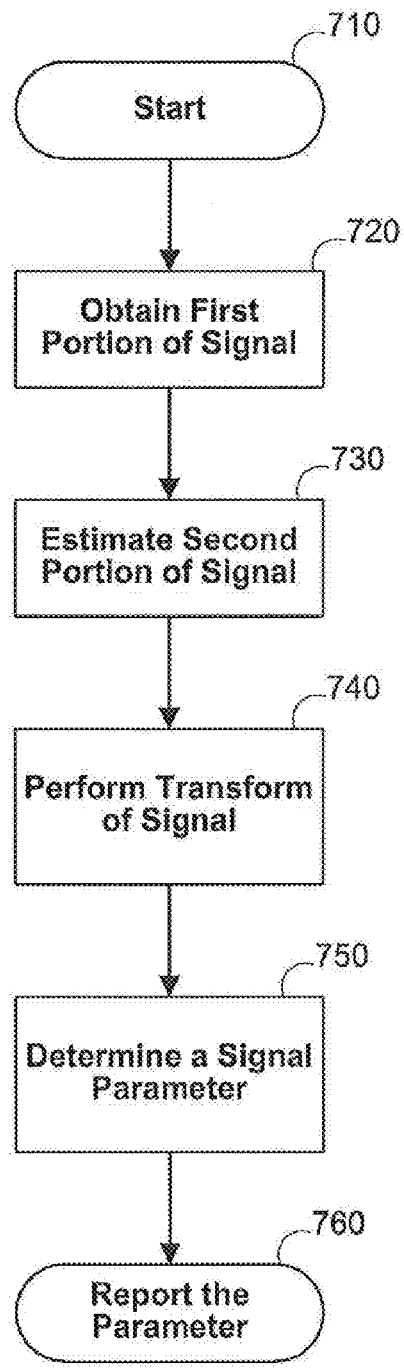
FIG. 7 depicts an illustrative process for determining parameters of a signal using estimated transform values generated from signal estimates in accordance with some embodiments.

FIG. 7 depicts an illustrative process 700 for determining parameters of a signal using estimated transform values generated from signal estimates. Process 700 may be implemented in a pulse oximetry system such as pulse oximetry system 10 (FIG. 1), and the steps of process 700 may be carried out using a processor such as processor 412 (FIG. 4) or microprocessor 48 (FIG. 2).

Process 700 may start at step 710. At step 720, a first portion of a signal may be obtained. The first portion of the signal may be a portion of a PPG signal or any other suitable biosignal or general signal. For example, the signal portion may be obtained from pulse oximetry system 10 (FIG. 1) using a sensor such as sensor 12 (FIG. 1) to measure biological parameters of a patient such as patient 40 (FIG. 2). Alternatively, the signal may be obtained by averaging or otherwise combining multiple signals derived from a suitable sensor array, as discussed in relation to FIG. 1. Further, the signal may be obtained from a source other than pulse oximeter system 10 (FIG. 1). For example, a signal may be obtained from another type of medical device or from non-medical devices including a general signal oscilloscope and/or waveform analyzer.

The signal obtained in step 720 may be obtained by processing a preliminary signal. For example, a preliminary PPG signal may be obtained using, e.g., sensor 12 (FIG. 1) and processed using a processor such as processor 412 (FIG. 4) or microprocessor 48 (FIG. 2) in a system similar or identical to pulse oximetry system 10 (FIG. 1). The signal obtained at step 720 may have been processed by methods including, for example, normalization, low-pass filtering, removal of noise-components, and/or interpolation methods to remove various undesirable artifacts that may be present in the preliminary signal.

At step 730 a second portion of the signal may be estimated. The portion of the signal obtained in step 720 may be a portion of a real-time signal or it may be a portion of a signal previously obtained and stored in memory, for example, ROM 52 (FIG. 2) or RAM 54 (FIG. 2) and that can be accessed and/or processed in real-time. Values for a portion of the signal that are not be currently known may be estimated. The estimated signal portion may include signal values that have not yet been received and/or processed. For example, the portion of the signal obtained in step 720 may represent a current portion of a real-time signal and the portion of the signal estimated in step 730 may represent future values of the signal. As another example, the portion of the signal obtained in step 720 may represent a generated signal and the portion of the signal estimated in step 730 may represent values of the signal that have not yet been generated. The estimated signal portion is not limited to signal values that follow the obtained signal portion, the unavailable portion may also include, for example, values of prior portions that were never obtained or that are no longer available.

Furthermore, the second signal portion estimated in step 730 may be a signal portion associated with obtained values that are obscured by signal noise and/or artifacts (including, for example, portion of the signal obtained in step 720). For example) a PPG signal may contain erroneous or otherwise undesirable artifacts due to, for example, patient movement, equipment failure, and/or various noise sources. For example, cable 24, cable 32, and/or cable 34 (all of FIG. 1) may malfunction or become loosened from the equipment to which it is connected. Further, sensor 12 (FIG. 1), or any constituent component of sensor 12 (FIG. 1) (for example, emitter 16 (FIG. 1) and/or detector 18 (FIG. 1)) may malfunction and/or become loosened. Additionally, noise sources may produce inconsistent features in a PPG signal or other biosignal. Possible sources of noise include thermal noise, shot noise, flicker noise, burst noise, and/or electrical noise caused by light pollution. These and other noise sources may be introduced, for example, through sensor 12 (FIG. 1), and/or cables 24, 32, and 34 (all of FIG. 1). These and/or other phenomena may be present in a system such as pulse oximetry system 10 (FIG. 1), and thus may introduce inconsistent features into a PPG signal.

At step 730 values for the second portion of the signal, corresponding to an unknown or erroneous portion of the signal, may be estimated based on the values of the portion of the signal obtained in step 720. The second portion of the signal may be estimated as a constant value, as an extrapolation of previous signal values, or may be estimated using any other suitable approach. Alternatively and/or additionally, where the second portion of the signal corresponds to obtained signal values that are obscured by noise or artifacts, the second portion of the signal may be estimated by filtering, interpolating or smoothing the obtained values of this signal portion to minimize the effects of these undesirable signal elements. These and other estimation techniques may be implemented in pulse oximetry system 10 (FIG. 1) by processor 412 (FIG. 4), microprocessor 48 (FIG. 2), ROM 52 (FIG. 2), and/or RAM 54 (FIG. 2). A plot the signal portions may be displayed using any suitable display device such as, for example, monitor 20 (FIG. 1), display 28 (FIG. 1), a PDA, a mobile device, any other suitable display device, or multiple display devices. An illustrative process for estimating a portion of the signal in step 730 is described in greater detail below with respect to FIG. 8.

At step 740 the signal portions obtained in steps 720 and 730 may be transformed (e.g., using a continuous wavelet transform). As described above with respect to FIG. 5 and FIG. 6, using the values of the signal portion estimated in step 730 to compute the transform of the signal portion obtained in step 720 may reduce the erroneous energy levels generated within the transform. The erroneous energy portions within the edge effect regions (or any other regions of the transform affected by unknown or erroneous signal data) may be replaced by estimated transform values. The transformation of the signal portions may be performed using, for example a processor such as processor 412 (FIG. 4) or microprocessor 48 (FIG. 2). An illustrative process for transforming the signal at step 740 is described below with respect to FIG. 9.

At step 750 one or more parameters of the signal may be determined from the transformed signal including the estimated transform values. For example, a PPG signal transformed in this manner may be used to determine a blood oxygen saturation value, a respiration rate, a respiration effort metric, or another suitable biological parameter. In an embodiment, a scalogram may be generated from the transformed signal using the same approach that was used to derive the scalograms shown in FIGS. 3(*a*), 3(*b*), 3(*c*), 5, and 6. The scalogram of the transformed signal may be generated or otherwise obtained using, for example a processor such as processor 412 (FIG. 4) or microprocessor 48 (FIG. 2). In addition to the scalogram, other parts of the wavelet transform may be determined. For example, the transform modulus, phase, real, and/or imaginary parts may be generated in addition to the scalogram. The generated scalograms may be displayed, for example, on monitor 26 (FIG. 1) or display 20 or 28 (both of FIG. 1).

The resultant scalogram may include bands and ridges corresponding to at least one area of increased energy. For example, a respiration band of the scalogram may generally reflect the breathing pattern of a patient, e.g., patient 40 (FIG. 2). These bands may be extracted from the scalogram using, for example, a processor such as processor 412 (FIG. 4) or microprocessor 48 (FIG. 2), using any suitable method. The respiration band of the scalogram may be identified using characteristics of the scalogram including the energy and structure of the scalogram, and the signal-to-noise levels in various regions of scalogram. One or more of the parameters may be determined at step 750 from the identified characteristics of the scalogram.

Finally, at step 760 the signal parameters determined in step 750 may be reported. For example, the parameters may be reported by generating an audible alert or, for example, using speaker 22 (FIG. 2) as well as possibly through other audio devices, generating an on-screen message, for example, on display 20 (FIG. 1) or display 28 (FIG. 1), generating a pager message, a text message, or a telephone call, for example, using a wireless connection embedded or attached to a system such as system 10 (FIG. 1), activating a secondary or backup sensor or sensor array, for example, connected through a wire or wirelessly to monitor 14 (FIG. 1), or regulating the automatic administration of medicine, for example, which is controlled in part or fully through a system such as system 10 (FIG. 1). Additionally, the signal parameters may be reported on a display such as display 20 (FIG. 1) or display 28 (FIG. 1) in graphical form using, for example, a bar graph or histogram. The signal parameters may also be reported to one or more other processes, for example, to be used as part of or to improve the reliability of other measurements or calculations within a system such as pulse oximetry system 10 (FIG. 1).

Figure 8:
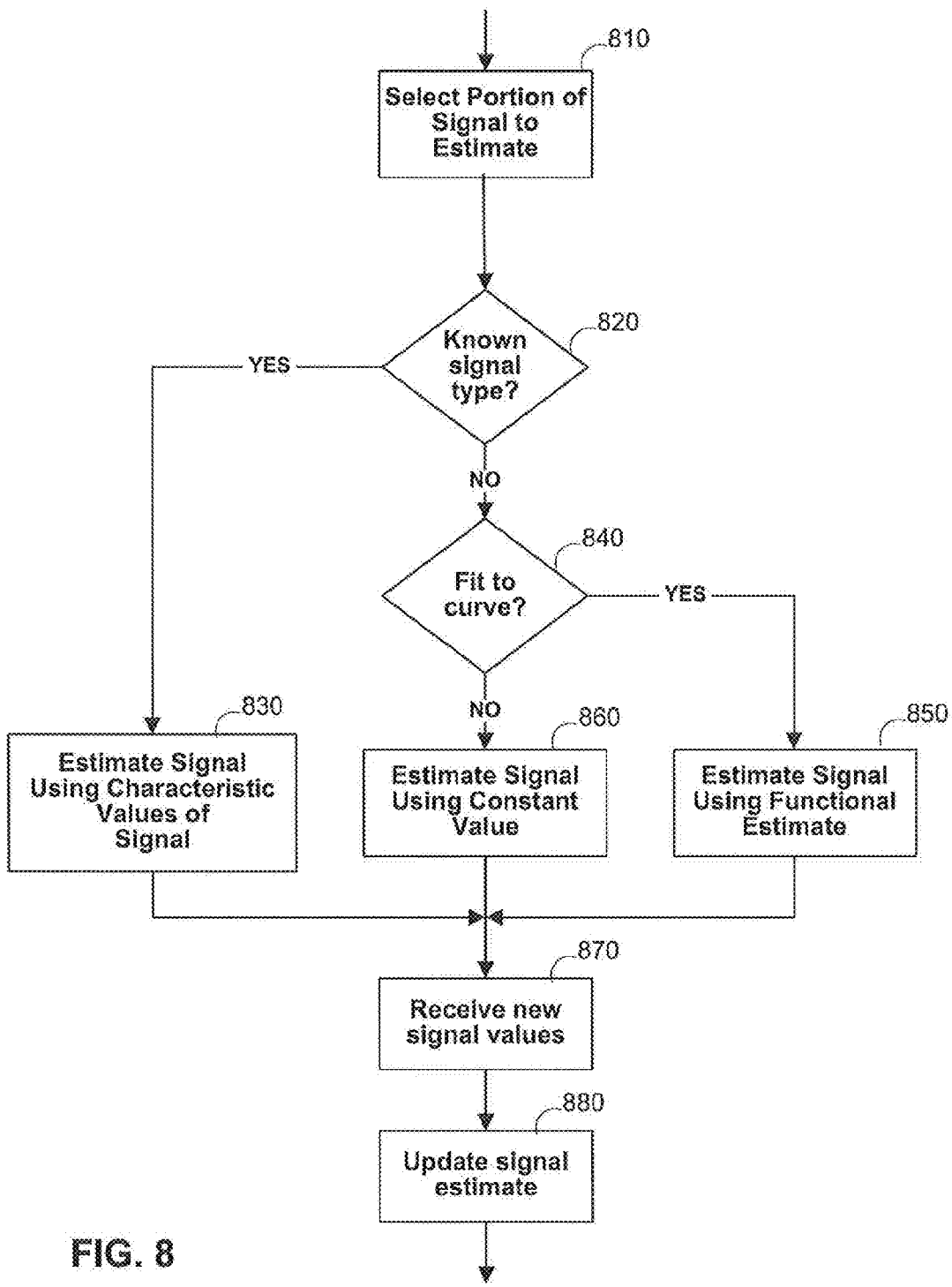
FIG. 8 depicts an illustrative process for estimating the values of a portion of a signal in accordance with some embodiments.

FIG. 8 depicts an illustrative process 800 for estimating the values of a portion of a signal. Process 800 may be implemented in a pulse oximetry system such as pulse oximetry system 10 (FIG. 1) to estimate a portion of a PPG signal, and the steps of process 800 may be carried out using a processor such as processor 412 (FIG. 4) or microprocessor 48 (FIG. 2). Process 800 may correspond to a further embodiment of a portion of process 700 (FIG. 7), and more particularly, may correspond to a further embodiment of step 730.

Process 800 may start at step 810. At step 810, a portion of a signal may be selected for estimation. The selected signal portion may be an unknown portion of the signal such as a portion of the signal that is not available or that has not yet arrived (i.e., a future or past signal portion). The selected signal portion may also be a portion of the signal that is obscured by noise and/or artifacts. In an embodiment, the signal portion may be selected based on a scalogram generated from the signal. For example, the selected portion of the signal may correspond to a region of the scalogram that has erroneous values such as an edge effect region. After the region of the scalogram is identified, a signal portion corresponding to that region may be selected for estimation.

The signal portion selected for estimation at step 810 may be selected automatically. For example, a portion of the signal that follows the leading edge of the signal may be selected automatically for estimation. As another example, a noisy or otherwise obscured portion of the signal may be selected automatically for estimation. These and other techniques may be implemented in pulse oximetry system 10 (FIG. 1) by processor 412 (FIG. 4), microprocessor 48 (FIG. 2), ROM 52 (FIG. 2), and/or RAM 54 (FIG. 2). Additionally, the parameters that may be used to select a signal portion for estimation may be controlled by a user or patient, e.g., using user inputs 56 (FIG. 2). The signal portion selected for estimation may be displayed, for example, on monitor 26 (FIG. 1) or display 20 or 28 (both of FIG. 1). Alternatively, a signal may be displayed on a monitor, and a user may choose or otherwise influence which portion of the signal (including unknown portions of the signal) is selected using, for example, user inputs 56 (FIG. 2). While process 800 is described primarily with respect to a single estimated signal portion, it should be understood that multiple signal portions may also be selected for estimation in accordance with this process.

At step 820 the known portions of the signal may be analyzed to determine whether the signal is a known signal type. The type of signal may be determined based on the type of system and/or sensor used to obtain the signal. For example, the signal received by pulse oximetry system 10 (FIG. 1) may be determined to be a PPG signal. The signal type may also be determined based on the characteristics of the signal. For example, the signal may be determined to be a PPG signal based on the size, shape, or frequency of the signal. These and other techniques may be implemented in pulse oximetry system 10 (FIG. 1) by processor 412 (FIG. 4), microprocessor 48 (FIG. 2), ROM 52 (FIG. 2), and/or RAM 54 (FIG. 2). For example, the signal analyzed in step 820 may be compared with a library of known signal types that may be stored in ROM 52 (FIG. 2), and/or RAM 54 (FIG. 2) by processor 412 (FIG. 4) and/or microprocessor 48 (FIG. 2). Additionally, the signal type may be selected by a user or patient using, e.g., using user inputs 56 (FIG. 2).

If it is determined at step 820 that the signal is a known signal type, at step 830 values of the signal portion selected in step 810 may be estimated. The values of the signal portion selected in step 810 may be estimated at step 830 by determining characteristic values of the known signal portions and estimating signal values based on the characteristic values of the known signal type. For example, if the signal is a PPG signal, values of the signal portion selected in step 810 may be estimated based on the characteristic values of the signal such as the size, shape and/or rate of the pulses in the PPG signal. If one or more of the determined characteristic values of the signal are determined to be stable, those values may be used to estimate the values of the selected signal portion of the PPG signal. For example, if the pulse size and shape of a PPG signal are determined to be stable but the pulse rate is not stable, only the characteristic values of the pulse size and shape may be used to estimate the values of the selected signal portion. According to this example, if the known portion of a PPG signal ends in the middle of a pulse, the values for the following portion of the signal may be estimated using the characteristic values of the shape and size of the pulse. Additionally and/or alternatively known signal types may be estimated based on information about the origin of the signal. For example, if the signal is a PPG signal information about typical pulse sizes and pulse rates may be used to help estimate the signal. Further, information obtained from other biosignals having known relationships to a PPG signal may also be used to estimate the signal. If values for the selected signal portion cannot be estimated using this technique, the signal values may be estimated using the techniques described below with respect to steps 850 and 860 or by using any other suitable estimation techniques.

If it is determined at step 820 that the signal is not a known signal type, at step 840 it is determined whether the signal fits a curve or any other type of function. If it is determined at step 840 that the signal fits a curve, signal values may be estimated at step 850 using an extrapolated estimate or fitted curve (i.e., a functional estimate) to estimate the signal. This determination may use, for example, self-optimizing/predictive neural networks, the projection of ensemble averaged historic data, non-linear extrapolation of historic data (e.g., through cubic spline fitting or other multi-order estimates), or any other suitable techniques. If these techniques are not sufficient to estimate the values for the selected signal portion, the values of the selected signal portion may be estimated using the techniques described below with respect to step 860 or any other suitable estimation technique.

If it is determined at step 840 that the signal cannot be fit to a curve or other function, at step 860 values of the signal portion selected in step 810 may be estimated as a constant value. The estimated constant value may be, for example, a known signal value closest in time to the signal portion selected for estimation in step 810, a mean or median value of the know portions of the signal, or any other suitable value. In an alternative embodiment, the signal may be estimated to approach a constant value (e.g., its mean value) smoothly over time. This may be advantageous in avoiding sudden transient features and discontinuities in the estimated signal. These and other signal estimation techniques may be implemented in pulse oximetry system 10 (FIG. 1) by processor 412 (FIG. 4), microprocessor 48 (FIG. 2), ROM 52 (FIG. 2), and/or RAM 54 (FIG. 2). Additionally, the techniques used to estimate the signal portion and/or the parameters of the estimation may be controlled by a user or patient, e.g., using user inputs 56 (FIG. 2).

In addition to estimating values for a selected signal portion, a confidence value may also be determined in accordance with process 800. The confidence value may represent a relative confidence in an accuracy of the determination. The confidence value may be represented by a number from 1 to 100, where a larger number indicates a high confidence value in the estimation (any other suitable number range could be used instead). The confidence value may be determined based on the length of the signal portion to be estimated, the length of the known signal portions used to estimate the signal values, the technique used to estimate the signal values, a determination of the accuracy of the estimation, etc. The confidence value may also be determined based on the determined accuracy of estimated transform values obtained from the estimated signal portion (e.g., at step 740 of FIG. 7) and/or based on actual values of the estimated signal portion when they become available.

At step 870 new signal values may be received. The received signal values may correspond to some of the values signal estimated in steps 830, 850, and 860. The estimated signal values may be replaced with the received values. At step 880 the estimated signal values that were not replaced with received signal values in step 870 may be updated with new estimates based on the received values. In addition to using the received signal values to update the estimated values, the estimation technique may be modified based on a comparison of the previously estimated values and the received values. If desired, process 800 may return to step 810 to select new signal portions for estimation after the previously selected portion is updated with received signal values. The steps for determining an estimation technique (i.e., steps 820 and 840) may be repeated or the same technique used for the previously selected portions may be used (as updated based on step 890, if applicable).

Figure 9:
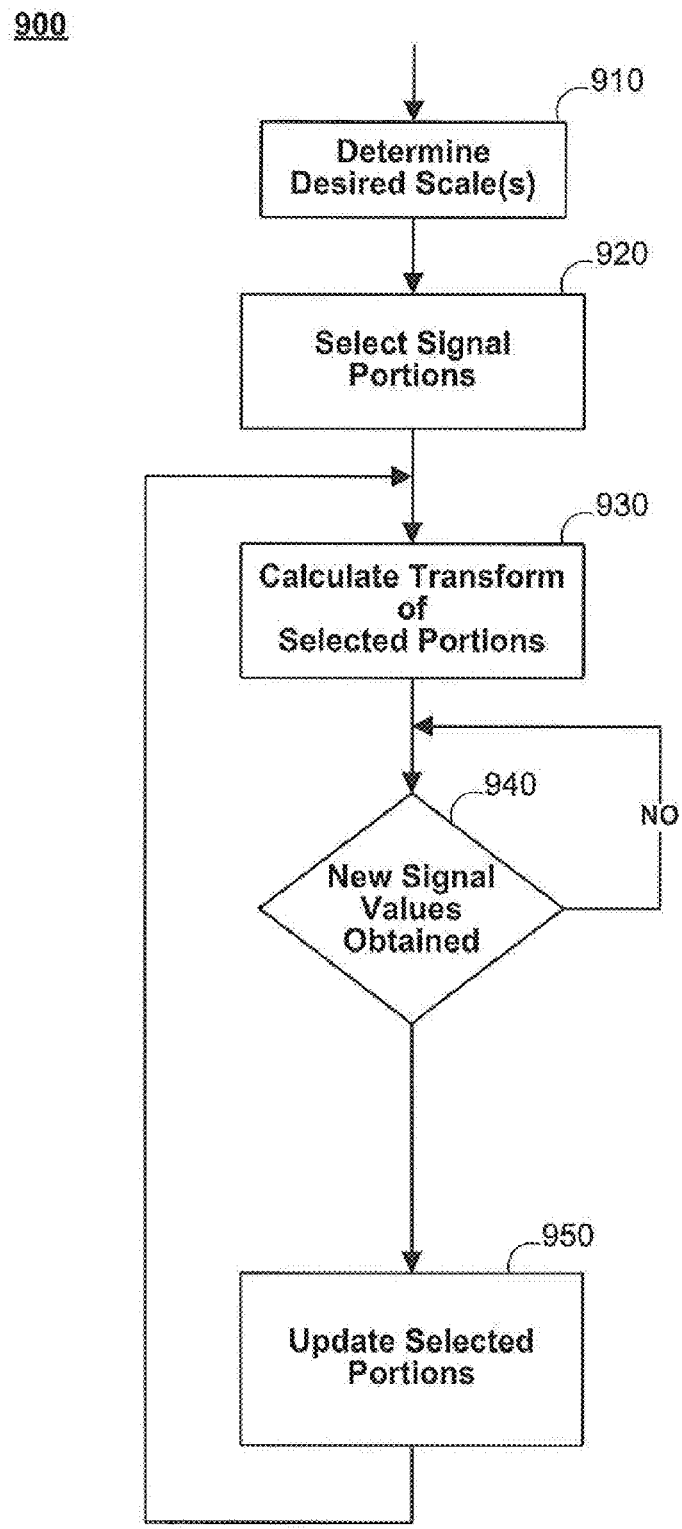
FIG. 9 depicts an illustrative process for performing a transform of a signal using estimated portions of the signal in accordance with some embodiments.

FIG. 9 depicts an illustrative process 900 for performing a transform of a signal using estimated portions of the signal. Process 900 may be implemented in a pulse oximetry system such as pulse oximetry system 10 (FIG. 1) to perform a continuous wavelet transform on a PPG signal including estimated signal portions, and the steps of process 800 may be carried out using a processor such as processor 412 (FIG. 4) or microprocessor 48 (FIG. 2). Process 900 may correspond to a further embodiment of a portion of process 700 (FIG. 7), and more particularly, may correspond to a further embodiment of step 740.

Process 900 may start at step 910. At step 910 desired scales for the transform may be determined. The desired scales may correspond to the entire range of scales within a scalogram (e.g. the range of scales displayed within FIGS. 5 and 6). The desired scales may also correspond to a range of scales associated with a particular feature or parameter that is being determined. For example, the desired bands of a PPG transform may correspond to the scales associated with pulse or respiration features. This determination of scales may be implemented in pulse oximetry system 10 (FIG. 1) by processor 412 (FIG. 4), microprocessor 48 (FIG. 2), ROM 52 (FIG. 2), and/or RAM 54 (FIG. 2). A scalogram of the signal may be displayed, for example, on monitor 26 (FIG. 1) or display 20 or 28 (both of FIG. 1) and a user or patient may choose or otherwise influence which scales within the scalogram are selected using, for example, user inputs 56 (FIG. 2).

At step 920 portions of a signal are selected based on the scales determined in step 910. The portions of the signal selected at step 920 include signal portions associated with known signal values (e.g., a portion of a signal obtained in step 720 (FIG. 7)) and signal portions associated with estimated signal values. The selected signal portions may include signal portions associated with known signal values that may be used to compute a transform of the signal at the desired scales. The selected signal portions may also include signal portions associated with estimated signal values that may be used together with the known signal values to compute a transform of the signal at the desired scales. As illustrated above with respect to FIGS. 5 and 6, at higher scales the smaller wavelet sizes may be used to compute a transform of a signal for a given time period using a relatively smaller portion of the signal than would be required to compute a transform of the signal for the same time period with the larger wavelet sizes at lower scales. This relationship between scale and signal portion size may be illustrated by the edge effect regions of FIGS. 5 and 6 in which signal edges (and the corresponding lack of additional signal values beyond the edges) are shown to cause larger edge effect regions at the lower scales. Therefore for a given time period the size of the selected estimated signal portions may depend on the desired scales selected in step 910. The values for the selected estimated signal portions may be determined) for example, in accordance with process 800 (FIG. 8). This selection of signal portions may be implemented in pulse oximetry system 10 (FIG. 1) by processor 412 (FIG. 4), microprocessor 48 (FIG. 2), ROM 52 (FIG. 2), and/or RAM 54 (FIG. 2). A plot of the signal and/or a scalogram of the signal may be displayed, for example) on monitor 26 (FIG. 1) or display 20 or 28 (both of FIG. 1) and a user or patient may choose or otherwise influence which portions of the signal are selected using, for example, user inputs 56 (FIG. 2).

At step 930 a transform of the signal portions selected in step 920 may be performed. For example, the selected signal portions may be transformed using a continuous wavelet transforms. As described above, using the estimated signal portions to compute the transform may reduce the erroneous energy generated within the transform. The erroneous energy portions within the edge effect regions (or any other regions of the transform effected by unavailable or poor signal data) may be replaced by estimated transform values. The transformation of the signal portions may be performed using, for example a processor such as processor 412 (FIG. 4) or microprocessor 48 (FIG. 2). A scalogram may be generated from the transformed signal portions using the same approach that was used to derive the scalograms shown in FIGS. 3(*a*), 3(*b*), 3(*c*), 5, and 6. The scalogram of the transformed signal may be generated or otherwise obtained using, for example a processor such as processor 412 (FIG. 4) or microprocessor 48 (FIG. 2).

At step 940 process 900 may wait to obtain new values for the signal. If new signal values are obtained, the selected portions of the signal may be updated at step 950. The new values may be used to replace previously estimated signal values. The new values may also be used to update or improve the estimated values for portions of the signal whose values are still unknown. The new values may also be used to estimate additional signal portions. For example, a sliding window (e.g., corresponding to an edge effect region of a range of scales) may be used to estimate signal portions for a particular time period following the last known signal value. As new values of the signal are obtained this window may advance to a next portion of the signal. Process 900 may then continue to transform of the updated signal portions at step 930. In an embodiment, a transform of the entire updated signal portions may be calculated. In an embodiment, only a transform of the updated values may be calculated and the previously calculated transform values may be updated with the newly calculated transform values. These and other techniques may be implemented in pulse oximetry system 10 (FIG. 1) by processor 412 (FIG. 4), microprocessor 48 (FIG. 2), ROM 52 (FIG. 2), and/or RAM 54 (FIG. 2).

It will also be understood that the above method may be implemented using any human-readable or machine-readable instructions on any suitable system or apparatus, such as those described herein.

What is claimed is:

1. A method for estimating transform values using a signal estimate comprising:
    obtaining a first portion of a biological signal from a sensor;
    estimating a second portion of the signal based at least in part on the first portion of the signal;
    performing a transform of the signal based at least in part on the first portion of the signal and the second portion of the signal; and
    determining a biological parameter corresponding to the signal based at least in part on the transformed signal.

2. The method of claim 1 wherein the biological signal comprises a photoplethysmograph (PPG) signal and wherein the determined parameter comprises blood oxygen saturation level, respiration rate, respiration effort metric, pulse rate, and/or blood pressure.

3. The method of claim 1 wherein the transform comprises a continuous wavelet transform.

4. The method of claim 3 wherein estimating the second portion of the signal further comprises:
    selecting a range of scales for the continuous wavelet transform; and
    determining a length for the second portion of the signal based at least in part on the selected range of scales.

5. The method of claim 4 wherein selecting the range of scales for the continuous wavelet transform comprises locating one or more features within a continuous wavelet transform of the signal.

6. The method of claim 1 wherein estimating the second portion of the signal comprises:
    determining an amplitude value of the first portion of the signal;
    estimating the determined amplitude value as a constant value for the second signal.

7. The method of claim 1 wherein estimating the second portion of the signal comprises:
    fitting a function to the first portion of the signal; and
    estimating the second signal using the function.

8. The method of claim 1 wherein estimating the second portion of the signal comprises:
    determining that the first portion of the signal is a known signal type;
    determining one or more characteristic values of the first portion PPG signal; and
    estimating the second signal by generating a signal portion of the known signal type having at least one of the determined characteristic values.

9. The method of claim 1 further comprising determining an estimation confidence value for the second portion of the signal.

10. The method of claim 1 further comprising updating the transform of the signal in response to obtaining signal values corresponding to the second portion of the signal.

11. The method of claim 1 wherein the second signal portion is generally adjacent to an end of the first signal portion.

12. The method of claim 1 wherein the second signal portion is generally within the first signal portion.

13. A system for processing a signal to estimate transform values using a signal estimate, the system comprising:
    a sensor to receive data indicative of a biological signal;
    a processor coupled to the sensor, wherein the processor is capable of:
        obtaining a first portion of the received signal;
        estimating a second portion of the signal based at least in part on the first portion of the signal;
        performing a wavelet transform of the signal based at least in part on the first portion of the signal and the second portion of the signal; and
        determining a biological parameter generally corresponding to the signal based at least in past on the transformed signal.

14. The system of claim 13 wherein the biological signal comprises a photoplethysmograph (PPG) signal and wherein the determined parameter comprises blood oxygen saturation level, respiration rate, respiration effort metric, pulse rate, and/or blood pressure.

15. The system of claim 13 wherein the processor is further capable of:
    selecting a range of scales for the continuous wavelet transform; and
    determining a length for the second portion of the signal based at least in pail on the selected range of scales.

16. The system of claim 15 wherein selecting the range of scales for the continuous wavelet transform comprises locating one or more features within a continuous wavelet transform of the signal.

17. The system of claim 13 wherein the processor is further capable of:
    determining an amplitude value of the first portion of the signal;
    estimating the determined amplitude value as a constant value for the second signal.

18. The system of claim 13 wherein the processor is further capable of:
    generally fitting a function to the first portion of the signal; and
    estimating the second signal using the function.

19. The system of claim 13 wherein the processor is further capable of:
    determining that the first portion of the signal is a known signal type;
    determining one or more characteristic values of the first portion PPG signal; and
    estimating the second signal by generating a signal portion of the known signal type having at least one of the determined characteristic values.

20. The system of claim 13 wherein the processor is further capable of determining an estimation confidence value for the second portion of the signal.

* * * * *